United States Patent [19]

Lyons et al.

[11] Patent Number: 5,705,685

[45] Date of Patent: Jan. 6, 1998

[54] CONVERSION OF ALKANES TO UNSATURATED CARBOXYLIC ACIDS

[75] Inventors: James E. Lyons, Wallingford; Paul E. Ellis, Jr., Downingtown; Swati Karmakar, Norristown; Shahid N. Shaikh, Media, all of Pa.

[73] Assignee: Sun Company, Inc. (R&M), Philadelphia, Pa.

[21] Appl. No.: 565,206

[22] Filed: Oct. 31, 1995

[51] Int. Cl.$^6$ .................................................. C07C 51/16
[52] U.S. Cl. ........................................................ 562/549
[58] Field of Search ............................................. 562/549

[56] References Cited

U.S. PATENT DOCUMENTS

| | | |
|---|---|---|
| 4,803,187 | 2/1989 | Lyons et al. . |
| 4,859,798 | 8/1989 | Lyons et al. . |
| 4,898,989 | 2/1990 | Ellis et al. . |
| 4,916,101 | 4/1990 | Lyons et al. . |
| 5,091,354 | 2/1992 | Ellis et al. . |
| 5,191,116 | 3/1993 | Yamamatsu et al. . |
| 5,334,780 | 8/1994 | Shaikh et al. . |
| 5,510,308 | 4/1996 | Kourtakis . |

FOREIGN PATENT DOCUMENTS

| | | |
|---|---|---|
| 0418657 | 3/1991 | European Pat. Off. . |
| 0425666 | 4/1994 | European Pat. Off. . |
| H242033 | 2/1990 | Japan . |
| H6218286 | 8/1994 | Japan . |

OTHER PUBLICATIONS

Pope et al., *Heteropoly and Isopoly Oxometalates*, 31–32 Springer Verlag, New York (1983).

Blake et al., *J.Chem.Soc. Dalton Trans.*, p.2509 (1985).

Uemura et al., *J.Chem.Soc. Dalton Trans.*, p.2565 (1973).

*Primary Examiner*—Paul J. Killos
*Attorney, Agent, or Firm*—Q. Todd Dickinson; Stephen T. Falk

[57] ABSTRACT

Alkanes are converted to unsaturated carboxylic acids by contacting an alkane with an oxidizing agent and a heteropolyacid or polyoxoanion comprising (1) at least 9 atoms of a first framework metal or metals comprising molybdenum, tungsten or vanadium or combinations thereof and (2) 1 to 3 atoms of a second framework metal or metals comprising zinc or a transition metal different from the first framework metal.

56 Claims, No Drawings

CONVERSION OF ALKANES TO UNSATURATED CARBOXYLIC ACIDS

FIELD OF THE INVENTION

This invention relates to the direct catalytic oxidation of alkanes to unsaturated carboxylic acids by the use of heteropolyacids or polyoxoanions.

BACKGROUND OF THE INVENTION

Heteropolyacids and Polyoxoanions

Heteropolyacids and polyoxoanions, both in general and those which can be used to prepare some of the catalysts used in our invention, and their preparation are thoroughly described in Pope et al., *Heteropoly and Isopoly Oxometalates*, Springer-Verlag, New York (1983).

In order to clarify the terminology used in the art, consider first a specific precursor to the catalyst of the present invention; $H_3PW_{12}O_{40}$. Since the cations in this composite are hydrogen, the compound is a heteropolyacid (HPA). If the cations were not all hydrogen, but either metals such as an alkali metal, potassium, sodium, or lithium, as in $K_3PW_{12}O_{40}$, or ammonium, as in $(NH_4)_3PW_{12}O_{40}$, then it is referred to as a polyoxoanion (POA).

As described in Pope et al., supra, heteropolyacids and polyoxoanions are cage-like structures with a primary, generally centrally located atom(s) surrounded by a cage framework, which framework contains a plurality of metal atoms, the same or different, bonded to oxygen atoms. The central element of heteropolyacids and polyoxoanions is different from metal atoms of the framework and is sometimes referred to as the "hetero" element or atom; the condensed coordination elements are referred to as the "framework" elements or metals. The framework metal atoms are ordinarily transition metals and have oxygen bonding such as:

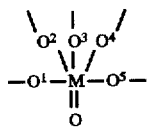

in which four of the singly-bonded oxygen atoms, for example, $O^1$, $O^2$, $O^4$ and $O^5$ are further bonded to other M atoms in the framework, and the fifth, for example $O^3$, is bonded to the central hetero atom.

The principal framework metal, M, is effectively limited to only a handful of metals including molybdenum, tungsten, vanadium, niobium and tantalum. According to Pope et al., supra, this is due to the necessary condition that suitable metals have appropriate cation radius and be good oxygen pπ-electron acceptors. Among the successful candidates, molybdenum and tungsten share a common feature; namely, the expansion of valences of their metal cations from four to six. The coincidence of these characteristics allow these metals to form stable heteropolyacids and polyoxoanions.

Conventional heteropolyacids (and polyoxoanions thereof) can be described by the general formula $H_e(X_kM_nO_y)^{-e}$. In this formula, X, the central atom, is frequently phosphorus. However, other suitable central atoms include Group IIIB-VIB elements, such as antimony, silicon and boron. Further, the subscript k is preferably 1, but can be as high as 5. M is molybdenum, tungsten, or vanadium and n will vary from 5–20. The subscript y is usually about 40, but can be as low as 18 or as high as 62. The notation e is the valence of the $(X_kM_nO_y)$ group and will vary from case to case, but e is always the number of H atoms needed to balance the formula. In a typical such heteropolyacid, k=1, n=12 and y=40 as in $H_3PMo_{12}O_{40}$ and the polyoxoanion $K_4PW_{11}VO_{40}$.

As described in Pope et al., supra, heteropolyacids are known to exist in a variety of structures including the Keggin, Dawson and Anderson structures. The different structures correspond to the specific geometry of particular heteropolyacid compositions and vary according to the coordination chemistry and atomic radii of the metals present.

Substituted Heteropolyacids and Polyoxoanions

We have earlier disclosed framework-substituted heteropolyacids and polyoxoanions which demonstrated improved activity for the conversion of alkanes to alcohols. Ellis et al., U.S. Pat. No. 4,898,989, issued Feb. 6, 1990. The improvement in catalyst activity was achieved by replacing certain framework atoms M (and the oxygen atoms doubly bonded to them) with zinc or transition metals or combinations thereof. The M atoms thusly replaced are best shown from the following structure:

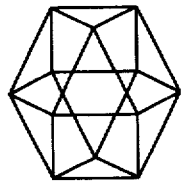

This twelve-cornered polyhedron structure is the metal atom cage-like configuration of a typical heteropolyacid described above. Between any two metal atoms of the framework of the cage is an oxygen atom, not shown, and from each metal atom is also a doubly-bonded oxygen not shown. Each of the metal atoms is bonded through oxygen to the central metal atom, not shown.

It can be seen from the diagram that eight of the fourteen faces of the above polyhedron are triangular and the other six are four-sided polygons. The M atoms which are replaced, according to our U.S. Pat. No. 4,898,989 patent, supra, are the three metal atoms in a single triangular face, not just any metal atoms as would happen in a random replacement. Another way of characterizing the regioselective, triangular insertion of the substituted metal atoms ("M'"), is that the M' atoms are each joined to each other in the above structural diagram (through oxygen atoms, if the complete structure were shown).

A typical heteropolyacid useful in making the subistituted compositions has the formula $H_3PMo_{12}O_{40}$. When three Mo=O units are replaced with, e.g. iron (Fe), the resulting framework substituted heteropolyacid has the formula $H_6PMo_9Fe_3O_{37}$. Thus, the general formula of the regioselectively substituted heteropolyacids described above becomes:

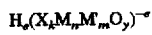

where k is 1–5, n is 5–19, m is 1–3 and y is 18–59. In this formula, M' comprises zinc or any of the transition metals, namely the Group IIIA-VIII metals of the periodic table. Preferably the transition metal is from Group VIII or the first row of Group IVA-VII, i.e., iron, cobalt, nickel, ruthenium, rhodium, palladium, osmium, iridium, platinum (Group VIII) or titanium, vanadium, chromium, managanese (IVA-VII, first row). Among the more preferred M' metals are iron, manganese, vanadium and combinations of nickel and iron or other transition metal. The three M' atoms do not have to be the same. However, the three M' must be different than the three M atoms replaced.

Preparation of Heteropolyacids and polyoxoanions

Heteropolyacids are conventionally prepared by dissolving the desired metal oxides in water, adjusting the pH to approximately 1–2 with acid (e.g. HCl) to provide the necessary $H^+$ cations, and then evaporating water until the heteropolyacid precipitates. If polyoxoanion is desired, a salt such as KCl is added. The polyoxoanion ordinarily precipitates without need for an evaporation step. The desired proportion of the metal oxides may vary somewhat from the theoretical amount required for the desired product. The existence of the heteropolyacid structure is confirmed by their characteristic NMR and/or IR spectra, which, as explained in Pope supra, are now known for various heteropolyacids.

In our U.S. Pat. No. 4,803,187, issued Feb. 7, 1989, we taught how to prepare heteropolyacids and polyoxoanions with random substitution of framework metals, such as $H_7(PMo_8V_4O_{40})$; $K_6(SiMo_{11}MnO_{39})$ and $K_5(PW_{11}VO_{40})$. The latter, for example, may be prepared by dissolving 45.0 g of 12-tungstophosphoric acid, $H_3(PMo_{12}O_{40})$, in 105 ml of water. With stirring the pH is adjusted to about 5.2 with potassium bicarbonate. The mixture is then heated to 70° C. and 6.0 g of vanadyl sulfate ($VOSO_4$) in 15 ml water is added. The solution is cooled and KCl is added to precipitate the $K_5(PW_{11}VO_{40})$ product.

The preparation of framework-substituted heteropolyacids or polyoxoanions as described in our U.S. Pat. No. 4,803,187 patent, supra, is adequate for random substitution, but will not provide the regiospecific, trilacunary substitution as described in our U.S. Pat. No. 4,898,989 patent, supra; i.e., replacement of three M in a single, triangular face with three M'. In order to achieve the latter, the following generalized procedures may be employed.

The overall procedure involves the reaction of a trilacunary polyoxoanion with a trimetalacetate, the metals of the latter being those to be inserted into the polyoxoanion. The framework substituted polyoxoanion is then converted to the corresponding heteropolyacid if desired. The trilacunary, $Na_9(PW_9O_{34})$, for example is prepared by mixing $Na_2WO_4$ and $H_3PO_4$ in the stoichiometric ratio in water at room temperature for 25 minutes and then slowly acidifying with 12N HCl to a final pH of 7.1. The $Na_9PW_9O_{34}$ precipitates and is separated. Other trilacunaries are prepared similarly by known analogous procedures.

It is apparent from the above that the $PW_9O_{34}$ in the trilacunary polyoxoanion represents the removal of three O—W=O units from the polyoxoanion and not merely W=O as described for the framework substituted heteropolyacid/polyoxoanion of our prior U.S. Pat. No. 4,803,187. This is merely a matter of satisfying the valences of tungsten (W) in the portion removed. The singly-bonded oxygen in the O—W=O is reinserted when M' is inserted so that the overall effect is the replacement of a M=O with M'; thus changing the number of framework oxygen atoms from 40 to 37.

The trimetal acetates have the general formula $M_3O(CH_3COO)_6(H_2O)_3$ where M is a transition metal or zinc and $M_3$ may be the same or different, e.g., $Fe_2NiO(CH_3COO)_6(H_2O)_3$. They are prepared, e.g., by reaction of appropriate salts. Thus the above diiron-nickel compound is prepared by mixing sodium acetate, iron nitrate, and nickel nitrate in acetic acid/$H_2O$ at room temperature and separating the precipitate. See Blake et al., *J. Chem, Soc. Dalton Trans.*, p. 2509 (1985); and Uemura et al., *J. Chem. soc. Dalton Trans.*, p. 2565 (1973).

Once the precursors are prepared, the framework substituted heteropolyacid/polyoxoanion is formed by reacting them together. For example, the trilacunary oxoanion $Na_9(PW_9O_{34})$ is dissolved in a pH 6, buffered KOAc/HOAc solution (OAc=acetate). Then an equimolar amount of the trimetal acetate, e.g., $Fe_2NiO(OAc)_6(H_2O)_3$ dissolved in water is added. After initial mixing, the mixture is stirred for one hour at 50° C. and then cooled to room temperature. KCl is added to precipitate the product $K_7(PW_9Fe_2NiO_{37})$. Various preparatory methods are described in Finke et al. *J.Amer.Chem.Soc.*, 108, p. 2947 (1986), F. Ortega, Ph.D. Thesis, Georgetown University (1982), and Domaille et al., *Inorg. Chem.*, 25, 1239–42 (1986).

The polyoxoanion salt can be readily converted to the acid form if desired. This is done by reacting an aqueous solution of the salt, e.g., $K_7PW_9Fe_2NiO_{37}$ at 50° C. for 15 minutes with an aqueous solution containing an excess of tetrabutylammonium bromide. Upon refrigeration at 4° C. overnight, the organic salt, $(nC_4N)_7PW_9Fe_2NiO_{37}$ crystallizes in 70% yield. The organic salt is filtered off and pyrolyzed at 500° C. for 1 hour. It turns into the black solid $H_7PW_9Fe_2NiO_{37}$ as confirmed by IR. The existence of the framework substituted heteropolyacid/polyoxoanion may be confirmed by IR and elemental analysis in known manner.

Regio-disubstituted heteropolyacids and polyoxoanions may be prepared similarly to the procedure described above. A dilacunary species, such as $K_8(SiW_{10}O_{36})$, is reacted at pH 3.8 with a dimeric metal formate, such as $[Cr_2(OH)(O_2CH)](TsO)_3$, where "TsO" is tosylate anion. The product of this reaction after purification is $K_8(SiCr_2W_{10}O_{38})$, where two W=O units have been replaced by two $Cr^{III}$ atoms.

Catalytic Oxidation

As described in Pope et al., heteropolyacids and polyoxoanions have found a variety of applications. In the area of catalysis, they have been used in connection with the oxidation of propylene and isobutylene to acrylic and methacrylic acids, oxidation of aromatic hydrocarbons; olefin polymerization; olefin epoxidation; acrylonitrile ammoxidation and hydrodesulfurization processes.

The use of heteropolyacids and polyoxoanions for the catalytic air oxidation of alkanes to alcohols, such as butane to butanol, is also known. See, for example, M. Ai, "Partial Oxidation of n-Butane with Heteropoly Compound-based Catalysts", *Proceedings of the 18th International Congress on Catalysis*, Berlin, 1984, Verlag Chemie, Vol. 5, page 475. In addition, we have previously disclosed the use of heteropolyacids and polyoxoanions under mild reaction conditions for the liquid phase oxidation of alkanes. See, Lyons et al., U.S. Pat. No. 4,803,187, supra. That patent is incorporated by reference herein.

Further, we have previously disclosed modified heteropolyacids and polyoxoanions, methods of preparation, and methods of use for oxidation of alkanes to alcohols. See, Lyons et al., U.S. Pat. No. 4,859,798, issued Aug. 22, 1989; Ellis et al., U.S. Pat. No. 4,898,989, supra; Lyons et al., U.S. Pat. No. 4,916,101, issued Apr. 10, 1990; Ellis et al., U.S. Pat. No. 5,091,354, issued Feb. 25, 1992; and Shaikh et al., U.S. Pat. No. 5,334,780, issued Aug. 2, 1994; all of which are incorporated herein by reference.

We have previously found that substitution of Group VIII and other transition metals as framework elements in a heteropolyacid or polyoxoanion catalyst enhances catalytic oxidation activity for the oxidation of alkanes to alcohols. See, Ellis et al., U.S. Pat. No. 4,898,989, supra; and Ellis et al., U.S. Pat. No. 5,091,354, supra.

Framework-substituted heteropolyacids similar to those described by Ellis et al. and Lyons et al., supra, were subsequently disclosed as catalysts for oxidation of aldehydes, cyclohexene and cyclohexane, and for hydrogen peroxide decomposition. N. Mizuno et al., "Synthesis of [PW$_9$O$_{37}${(Fe$_{3-x}$Ni$_x$(OAc)$_3$}]$^{(9+x)-}$ (x=predominantly 1) and Oxidation Catalysis by the Catalyst Precursors", *J.Mol.Cat.*, 88, L125–31 (1994); and Wu et al., "Catalytic Behavior of Metal Ions Located at Different Sites of Heteropoly Compounds", *Catalysis Letters*, 23, 195–205 (1994).

Production of Carboxylic Acids

Non-framework substituted polyoxometallates (heteropoly-acids and polyoxoanions) are known in the art as catalysts for oxidation of isobutane to methacrylic acid and methacrolein. N. Mizuno et al., "Direct Oxidation of Isobutane into Methacrylic Acid and Methacrolein over Cs$_{2.5}$Ni$_{0.08}$-substituted H$_3$PMo$_{12}$O$_{40}$," *J.Chem.Soc.,Chem. Commun.*, 1411–1412 (1994); S. Yamamatsu et al., "Process for Producing Methacrylic Acid and Methacrolein", European Patent Specification Publication No. 0 0 425 666 B1, application Ser. No. 89905775.6 filed May 22, 1989, Date of publication of patent specification Apr. 13, 1994; S. Yamamatsu et al., "Method for the Fabrication of Methacrylic Acid and/or Methacrolein", Japanese Patent Application Public Disclosure No. H2-42034, Feb. 13, 1990; S. Yamamatsu et al., U.S. Pat. No. 5,191,116, issued Mar. 2, 1993; K. Nagai et al., Process for producing methacrylic acid and methacrolein by catalytic oxidation of isobutane", European Patent Application Publication No. 0 418 657 A2, application Ser. No. 90117103.3, filed Sep. 5, 1990 by Sumitomo Chem. Ind. KK (published Mar. 27, 1991).

T. Jinbo et al., "Method for the Manufacture of Acroleic Acid or Acrylic Acid, and Catalysts Used Therein", Japanese Patent Application Public Disclosure No. H6-218286, Aug. 9, 1994, discloses the conversion of propane to acrolein and/or acrylic acid catalyzed by extra-framework metal substituted heteropolyacids; i.e., cation-exchanged heteropolyacids. A single framework mono-substituted heteropolyacid, H$_4$PMo$_{11}$VO$_{40}$, showed moderate selectivity for acrylic acid and poor conversion rate.

A heteropolyacid containing ten molybdenum atoms and two vanadium atoms randomly substituted in its framework has been disclosed as catalyzing the oxidation of n-butane to maleic anhydride, acrylic acid and acetic acid. M. Ai, "Partial Oxidation of n-Butane with Heteropoly Compound-based Catalysts", Labo. Resources Utiliz., Tokyo Inst. Tech., Yokohama, Japan, 8 *th International Congress on Catalysis, Volume V: Cluster-derived Catalysts, Active phase support interactions, catalysts for synthesis of Chemicals*, Verlag Chemie, Berlin, pages V475–V486 (1984).

G. Centi et al., "Selective Oxidation of Light Alkanes: Comparison between Vanadyl Pyrophosphate and V-Molybdophosphoric Acid", Catal.Sci.Technol., *Proc. Tokyo Conf.*, 1st Meeting, 1990, 225–30, 227, disclose that the randomly framework-substituted H$_5$PMo$_{10}$V$_2$O$_{40}$ has been found to be more active than (VO)$_2$P$_2$O$_7$ for catalyzing oxidation of propane to acrylic acid. However, the heteropolyacid was inactivated with 1.5 hours. The reported results may suggest that the H$_5$PMo$_{10}$V$_2$O$_{40}$ composition was not functioning as a catalyst, but was rather functioning as a stoichiometric reagent.

When a combination of the unsubstituted heteropolyacid, H$_3$PMo$_{12}$O$_{40}$, and V$_2$O$_5$—P$_2$O$_5$ is used to catalyze oxidation of propane to acrylic acid, this unsubstituted heteropolyacid is disclosed as enhancing the formation of acetic acid byproduct. M. Ai, "Oxidation of Propane to Acrylic Acid", *Catalysis Today*, 13(4), 679–684 (Eng.) (1992).

N. Mizuno et al., *Applied Catalysis A: General*, 128, L165–L170 (1995), reported that Fe$^{+3}$ or Ni$^{+2}$ exchange for H$^{3O}$; and V$^{+5}$ mono-substitution for Mo$^{+6}$ in Cs$_{2.5}$H$_{0.5}$PMo$_{12}$O$_{40}$ enhanced the catalytic activity for direct oxidation of propane to acrylic acid. Of the catalysts tested, Cs$_{2.5}$Fe$_{0.08}$H$_{0.5}$PMo$_{11}$VO$_{40}$ gave the highest yield of acrylic acid.

Ueda et al., *Chemistry Letters*, 541, 2 (1995), reported that propane was catalytically oxidized to acrylic acid and acetic acid with molecular oxygen over unsubstituted heteropolymolybdophosphoric acids which were treated with pyridine.

Cavani et al., *Catalysis Letters*, 32 215–226 (1995), reported that the addition of iron salts led to a substantial increase in the activity of unsubstituted 12-molybdophosphoric acid for the oxidation of isobutane to methacrylic acid.

The references cited above primarily employed non-framework substituted heteropolyacids as catalysts in manufacture of unsaturated carboxylic acids, for example acrylic acid and methacrylic acid, from alkanes, for example propane and isobutane. As noted, there has also been some use disclosed of heteropolyacids and polyoxoanions with random vanadium substitution of one or two framework metals. The yields and selectivities from the use of those random, mono-and divanadium-substituted heteropolyacids, described in the cited references was generally below the level required for a practical process. There has been no prior disclosure or use of site-specific, regioselective di-, tri- or multi-substituted heteropolyacids or polyoxoanions for the conversion of alkanes to unsaturated carboxylic acids.

Given the value and industrial importance of acrylic acid and methacrylic acid, it has been recognized that the one-step conversion of alkanes to unsaturated carboxylic acids would be a useful process with important commercial applications, provided that sufficient yield can be obtained. To date, no efficient catalysts have been developed for the commercial production of acrylic acid from propane or methacrylic acid from isobutane. As a result, acrylic acid is manufactured from propylene, a raw material which is over three times more expensive than propane.

The process of the present invention provides such a one-step process for the conversion of alkane to carboxylic acid. The advantages of the process according to the invention are that the higher catalytic activities of the catalysts used in the process allow the process to be carried out at lower temperatures than those used in the prior art, and to obtain higher reaction rates, yields and selectivities than those obtained in the prior art. These advantages make the process more attractive than the prior art processes for practical use and potential commercial interest.

It has been found that the yield and/or selectivity for unsaturated carboxylic acids in the partial oxidation of alkanes catalyzed by heteropolyacids and/or polyoxoanions, may be increased by substituting oxidation-active metals, for example iron, in Keggin and Dawson structures for Group VI metals, for example molybdenum, in the Keggin or Dawson structure to obtain superior catalysts for the direct oxidation of alkanes to unsaturated carboxylic acids, for example, acrylic or methacrylic acids.

SUMMARY OF THE INVENTION

The present invention relates to the oxidation of alkanes to unsaturated carboxylic acids catalyzed by heteropolyacids (HPAs) or polyoxoanions (POAs) which have been promoted or otherwise modified to improve their effectiveness. The process of the invention is useful, for example, for the conversions of propane to acrylic acid and isobutane to methacrylic acid. In one embodiment, the process of the present invention involves the conversion of alkane to unsaturated carboxylic acid at a temperature in the range of about 225° C. to 450° C. by contacting the alkane with an oxidizing agent in the presence of a heteropolyacid or polyoxoanion catalyst.

The invention comprises a process for the conversion of alkanes to unsaturated carboxylic acids which comprises contacting an alkane with an oxidizing agent under oxidation conditions with a heteropolyacid comprising (1) at least 9 atoms of a first framework metal or metals comprising molybdenum, tungsten, or vanadium or combinations thereof, and (2) at least one atom of a second framework metal or metals comprising independently zinc or a transition metal, other than molybdenum, tungsten or vanadium, or combination thereof; or polyoxoanion of said heteropolyacid.

The catalysts useful in the process of the present invention have the general formula $H_e(X_kM_mM'_nO_y)^{-e}$ where X, the central or hetero atom, is a Group IIIB, IVB, VB, VIB or transition element, such as phosphorus, silicon, gallium, aluminum, arsenic, germanium, boron, cobalt, cerium, praseodymium, uranium and thorium; M, the first framework metal is molybdenum, tungsten, vanadium or combinations thereof; M', the second framework metal, is different from M and is independently zinc or a transition metal, such as titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combination thereof; k is 1 to 5; m is 5 to 17; n is 1 to 3; y is 18 to 59; and e is the charge of the anion of the heteropolyacid; or a polyoxoanion of such heteropolyacid. When n is 1, M' is other than molybdenum, tungsten or vanadium.

The catalysts used in the process of the invention may be modified by supporting the heteropolyacid or polyoxoanion on silica or other known catalytic support. Such supported catalysts may be further modified by pretreatment with water and by formation in the presence of vanadyl sulfate.

Suitable cations of the polyoxoanions useful in the process of the invention comprise alkali metal, including, not limited to, potassium, sodium, cesium and the like; transition metal, such as vanadium, chromium, manganese, iron, cobalt, ruthenium, copper and the like; actinide metal; lanthanide metal; metal oxo moiety such as V=O ("vanadyl"), Cr=O ("chromyl"), U=O ("uranyl") and the like; or other cation such as ammonium, $R_4N^+$ ("tetraalkylammonium") and the like.

The conversion process is carried out at a temperature in the range from 225° C. to 450° C., preferably in the range from 275° C. to 400° C. The pressure used in the process of the invention is not critical and may, for example, may be atmospheric pressure or such other pressure as is within the ability of the person skilled in the art to determine.

DETAILED DESCRIPTION OF THE INVENTION

The present invention relates to the oxidation of alkanes to unsaturated carboxylic acids catalyzed by heteropolyacids (HPAs) or polyoxoanions (POAs) which have been promoted or otherwise modified to improve their effectiveness. The process of the invention is useful, for example, for the conversions of propane to acrylic acid and isobutane to methacrylic acid.

Reaction Conditions

The temperature used in the process of the invention is that which favors the formation of unsaturated carboxylic acids as reaction products. The conversion process is carried out a temperature in the range from about 225° C. to about 450° C. The process of the invention is typically performed at a temperature of at least about 225° C., and preferably at least about 275° C., and below that which will cause an undesirable level of decomposition of the starting material to carbon oxide and water. Preferably, the temperature is not above 450° C., more preferably not above 400° C. The determination of the most desirable temperature for a given reaction within the scope of the invention is within the ability of the person skilled in the art.

The pressure used in the process of the invention is not critical. The process may be carried out at atmospheric pressure. Other pressures may be used, and the determination of the most desirable pressure for a given reaction within the scope of the invention is within the ability of the person skilled in the art.

The process of the invention may be carried out in any suitable reactor configuration. For example, the reaction may be performed in a fixed-bed, moving bed, ebullating bed reactor, or other as is within the ability of the person skilled in the art to determine.

The process of the invention is preferably carried out in vapor phase. Preferably, the feedstock is an alkane gas. The reaction may be carried in the presence or absence of steam. An inert gas, such as nitrogen, argon, helium or the like, may also be used. When an inert, diluting gas is used in the process of the invention, determination of the molar ratio of alkane, oxidant, diluting gas and water (steam), if present, in the starting reaction gas mixture is within the ability of the skilled practitioner in the art. Determination of the gas space velocity used in the process of the invention is within the ability of the skilled practioner in the art.

Feedstocks

The alkane starting materials include straight and branched-chain compounds suitable for conversion to unsaturated carboxylic acids or combinations thereof. Preferred among these are light alkanes comprising three to seven carbon atoms. More preferred feedstocks for the process of the present invention are propane and isobutane which may be oxidized by the process of the present invention to form acrylic acid and methacrylic acid, respectively.

As noted above, the feedstock may comprise a combination of alkanes, preferably $C_3$–$C_7$ alkanes. In addition, the purity of the starting material is not critical. As a result, the feedstock may, in addition to the alkane or alkanes of interest, further comprise methane or ethane as well as impurities such as air or carbon dioxide.

Suitable oxidants for use in the process of the invention comprise air, molecular oxygen and other oxidants, such as nitrogen oxides. Preferred among these are air and molecular oxygen.

In one embodiment of the invention, an alkane is contacted with an oxidizing agent in the presence of a framework-substituted heteropolyacid or polyoxoanion catalyst. For example propane is contacted with an oxidizing agent in the presence of a framework-substituted heteropolyacid or polyoxoanion catalyst according to the invention, to produce acrylic acid. Similarly, isobutane is converted to methacrylic acid.

Catalyst

The catalysts useful in the process of the present invention comprise heteropolyacids or polyoxoanions which have been framework-substituted as described below. The substitution may, for example, be monosubstitution, regio-disubstitution or regio-trisubstitution, all of which produce active catalysts for such oxidation. The catalysts may be further promoted by a variety of means described below.

In one embodiment, the catalysts useful in the present invention have the general formula $H_e(X_kM_mM'_nO_y)^{-e}$ where X, the central or hetero atom, is a Group IIIB, IVB, VB, VIB or transition element, such as phosphorus, silicon, gallium, aluminum, arsenic, germanium, boron, cobalt, cerium, praseodymium, uranium and thorium; M, the first framework metal is molybdenum, tungsten, vanadium or combinations thereof; M', the second framework metal, is different from M and is independently zinc or a transition metal, such as titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combination thereof; k is 1 to 5; m is 5 to 17; n is 1 to 3; y is 18 to 59; and e is the charge of the anion of the heteropolyacid; or a polyoxoanion of such heteropolyacid. When n=1, the second framework metal, M', is other than molybdenum, tungsten or vanadium.

The catalysts useful in the process of the present invention may be promoted by various means including supporting the heteropolyacid or polyoxoanion on silica or other conventional catalyst support, pretreating supported heteropolyacid or polyoxoanion with water, and preparing the catalyst in the presence of vanadyl sulfate or the like. In addition, exchange of iron or other transition metals, actinide and lanthanide metals, and other cations has been found to promote the activity of the catalysts used in the process of the invention.

The invention comprises a process for conversion of alkanes to unsaturated carboxylic acids by contacting an alkane with an oxidizing agent under partial oxidation and dehydrogenation conditions with a heteropolyacid or polyoxoanion comprising (1) at least 9 atoms of a first framework metal or metals comprising molybdenum, tungsten, vanadium or combinations thereof and (2) at least one atom of a second framework metal or metals comprising zinc or a transition metal other than molybdenum, tungsten or vanadium, thereby to convert said alkane to an unsaturated carboxylic acid. When there is more than one second framework metal, they may comprise a combination of zinc and the available transition metals.

Preferably, the heteropolyacid or polyoxoanion used in the process of the invention comprises 9 to 11 atoms of a first framework metal selected from the group consisting of molydenum, tungsten and vanadium, and 2 to 3 atoms of a second framework metal such as titanium, zirconium, vanadium, niobium, tantalum, chromium, molybdenum, tungsten, manganese, rhenium, iron, cobalt, nickel, ruthenium, rhodium, palladium, osmium, iridium, platinum, copper or zinc, which second metal is zinc or a transition metal different from the first framework metal. The second framework metals (M') are site-specific, regioselective substitutions wherein each M' is bound through an oxygen atom to another M'.

The central or hetero element, X, of the heteropolyacid or polyoxoanion catalyst useful in the process of the present invention is selected from the elements of Group IIIB, IVB, VB, VIB of the Periodic Table or from the transition elements; it may, for example, be phosphorus, silica, aluminum, germanium or the like. The first framework element comprises molybdenum, tungsten, vanadium or the like. An example of such heteropolyacid is $H_3PW_{12-n}M'_nO_{40}$, in which phosphorus (P) is the hetero atom and tungsten (W) is the first framework metal and M' is the second framework metal as described below.

The heteropolyacid or polyoxoanion used in the process of the invention contains second framework metals which have been substituted into the framework thereof, replacing an equivalent number of the first framework metals. Such substituting metals may, for example, be titanium, zirconium, hafnium, vanadium, niobium, tantalum, chromium, molybdenum, tungsten, manganese, rhenium, iron, cobalt, nickel, ruthenium, rhodium, palladium, osmium, iridium, platinum, copper, zinc or combinations thereof. The second framework metal (M') is, by definition, different from the first framework metal (M). When there are more than one M' atoms, each M' is bound through an oxygen atom to another M'.

The atoms which have been replaced in such substitution may be for example molybdenum, tungsten, vanadium or combinations thereof, as disclosed in Ellis and Lyons U.S. Pat. No. 4,898,989, supra. The number of framework atoms replaced may be from 1 to 3 or more, and the substituting metals, which are different from the replaced metal, may each be the same metal, for example iron, or may be different from each other, for example two or three different metal atoms; e.g., one iron atom may replace one tungsten atom; two iron atoms may replace two tungsten atoms; three iron atoms may replace three tungsten atoms; two atoms, different from each other, for example iron and cobalt, may replace two tungsten atoms; three atoms, different from each other, for example iron, cobalt and nickel, may replace three tungsten atoms; two atoms of iron and one atom of cobalt may replace three tungsten atoms; and so on. Replacement of three framework atoms of a heteropolyacid or polyoxoanion by three atoms, different from the framework atom, two of which replacing atoms are selected from the group consisting of iron, chromium, manganese or ruthenium, and the third of which is different from the two just referred to and is a transition metal, is disclosed in Lyons et al., U.S. Pat. No 5,091,354.

In addition, the catalyst used in this invention may be for example a heteropolyacid or polyoxoanion (collectively, a polyoxometallate) having the formula $H_cM''_b{}^{+a}(X_kM_mM''_nO_y)^{-e}$ where $c + (a \times b) = e$; a is the valence state of the cation M"; b is the number of M" units in the complex; and c is zero or an integer. M" may comprise alkali metal, including, not limited to, potassium, sodium, cesium and the like; transition metal, such as vanadium, chromium, manganese, iron, cobalt, ruthenium, copper and the like; actinide metal; lanthanide metal; metal oxo moiety such as V=O ("vanadyl"), Cr=O ("chromyl"), U=O ("uranyl") and the like; or other cation such as ammonium, $R_4N^+$ ("tetraalkylammonium") and the like.

Examples of such heteropolyacids, as disclosed in Lyons et al., U.S. Pat. No. 5,091,354, supra, are $H_6PW_9Fe_3O_{37} \cdot NaN_3$ wherein phosphorus (P) is the hetero atom, tungsten (W) is the first framework metal, and iron atom, tungsten (W) is the first framework metal; $H_7PW_9Fe_2MO_{37} \cdot NaN_3$, (Fe) is the second framework metal; $H_7PW_9Fe_2MO_{37} \cdot NaN_3$, wherein phosphorus (P) is the hetero atom, tungsten (W) is the first framework metal, and iron (Fe) and "M" are the second framework metals, M being variously nickel, manganese, cobalt, zinc; and $H_7PW_9Cr_3O_{37} \cdot NaN_3$, wherein phosphorus (P) is the hetero atom, tungsten (W) is the first framework metal, and chromium (Cr) is the second framework metal. Examples of such heteropolyacids, as disclosed in Hartwell et al., U.S. Pat. No. 4,983,735, supra, are $H_3PW_{10}M_2O_{40}$, where M is titanium, zirconium, niobium, tantalum, manganese, iron, cobalt, nickel or copper.

The heteropolyacid or polyoxoanion catalyst may additionally be supported on conventional catalyst support materials, such as silica, alumina, silica-alumina, carbon, zirconia, titania, ceria, magnesia or the like, preferably silica. It has been found that the activity of the catalyst is increased when the catalyst is so supported. In addition, pretreatment of the supported catalyst with water has been found to increase acrylic acid production as has preparation of the catalyst in the presence of vanadyl sulfate.

In one embodiment of the invention, the heteropolyacid or polyoxoanion may usefully be supported on a conventional catalyst support, such as silica, alumina, silica-alumina, carbon, zirconia, titania, ceria, magnesia, or the like. Supported catalysts with catalyst loading of approximately 30 weight percent (i.e., 30 wt.% HPA and 70 wt.% support) were prepared by standard aqueous incipient wetness techniques. Modification of this ratio for purposes of manipulating the activity or other characteristics of the catalyst or the process is within the ability of the practitioner of the art. The amount of heteropolyacid or polyoxoanion and support used to prepare the supported catalyst may be varied according to the pore volume of the support and the degree of catalyst loading desired. These supported catalysts may be prepared, for example, by spraying the heteropolyacid or polyoxoanion dissolved in water onto the dried support or by means known in the art. Preferably, the supported catalyst is dried and calcined prior to use.

In one embodiment of the invention, the supported heteropolyacid or polyoxoanion may be pre-treated with water. The catalyst was prepared by exposure to air saturated with water vapor for approximately 48 hours. The hydrated catalyst may comprise about 5 to 30 weight percent water. This pretreatment of the catalyst by hydration was found to enhance catalytic activity.

In one embodiment of the invention, the supported heteropolyacid or polyoxoanion may be prepared in the presence of vanadyl sulfate ($VOSO_4$). The catalyst was prepared by mixing heteropolyacid and $VOSO_4$ and then applying the mixture to a silica support. The supported catalyst was then dried and calcined prior to use.

EXAMPLES

The following examples serve to illustrate embodiments of the present invention:

Example 1

We prepared supported heteropolyacid catalysts for use in the conversion of propane to acrylic acid. The heteropolyacids used were $H_4PMo_{11}VO_{40}$, $H_5PMo_{10}V_2O_{40}$, and $H_6PMo_9V_3O_{40}$.

Prior to catalyst preparation, 18/35 mesh $SiO_2$ pellets were heated in an oven for 6 to 8 hours at an elevated temperature in the range from 300° C. to 500° C. to remove any adsorbed impurities from the surface. Incipient wetness technique was used to support the heteropolyacid on the $SiO_2$ surface.

A given weight of $SiO_2$ pellets was measured and the pore volume of the pellets was calculated from the BET pore volume of the $SiO_2$ support (1.2 ml/g). Based on the desired catalyst loading, e.g. 30wt%, an appropriate amount of heteropolyacid was weighed in a beaker. The heteropolyacid was dissolved in an approximately 25% excess of water based on the total pore volume of the support since the external surface of the $SiO_2$ pellets also adsorbs water. Acetonitrile could optionally be used to dissolve the heteropolyacid. The water was added to the beaker and the heteropolyacid dissolved with the aid of a magnetic stirrer. The resulting solution was then sprayed evenly on the $SiO_2$ support using a syringe. The supported catalyst was then dried in a furnace at 130° C. for 6 hours, followed by calcination at 325° C. to 350° C. for 3 to 6 hours. When acetonitrile is used to dissolve the heteropolyacid, the drying step was carried out at 50° C.

Example 2

The $SiO_2$-supported heteropolyacids as prepared in Example 1 were further modified by pre-treatment with water for use according to one embodiment of the invention.

Supported heteropolyacids $H_4PMo_{11}VO_{40}/SiO_2$, $H_5PMo_{10}V_2O_{40}/SiO_2$, and $H_6PMo_9V_3O_{40}/SiO_2$ prepared as in Example 1 were placed in a tubular Pyrex reactor furnished with a fritted glass. Air saturated with water vapor at an approximate flow rate of 300 ml/minute was passed through the fixed bed of catalyst for approximately 48 hours. The air was first saturated with water vapor by bubbling it through an impinger containing water at room temperature.

TGA analyses were later carried out to determine the total water content of the pre-treated catalysts. The water content of the catalysts was as follows: $H_4PMo_{11}VO_{40}/SiO_2/H_2$—5 wt%; $H_5PMo_{10}V_{40}/SiO_2/H_2O$—28 wt%, and $H_6PMo_9V_3O_{40}/SiO_2/H_2O$—27 wt%. As determined by IR and XRD, the passage of water vapor appeared to reconstruct the Keggin structure which had been partially decomposed during calcination and also appeared to improve the dispersion of the heteropolyacid on the $SiO_2$ support.

Example 3

$SiO_2$-supported catalyst as prepared in Example 1 was modified for use in one embodiment of the process of the present invention by preparing the catalyst in the presence of vanadyl sulfate ($VOSO_4$).

Initially, 4.04g of 18/35 mesh $SiO_2$, which had been predried at 300° C., was weighed in a Pyrex dish. This sample of $SiO_2$ was calculated to have a pore volume of 6 ml.

Since it was desired to produce a catalyst with a final loading of 30 wt%, i.e., 30 wt% catalyst and 70 wt% support, 1.75g of $H(VO)_2(PV_2Mo_{10}O_{40})$ was needed. The mole ratio of vanadyl to heteropolyacid being 2:1, 1.62g of $H_5(PV_2Mo_{10}O_{40})$ and 0.41g of $VOSO_4 \cdot 3H_2O$ were used to prepare the $H(VO)_2(PV_2Mo_{10}O_{40})$ catalyst. 0.41 g of $VOSO_4 \cdot 3H_2O$ was dissolved in 6 ml of distilled water (corresponding to the pore volume of the support plus 25%) at room temperature using a magnetic stirrer. To that solution, was added 1.62 g of $H_5(PV_2Mo_{10}O_{40})$. The solution was sprayed evenly on the $SiO_2$ using a syringe.

The supported catalyst was dried in a furnace at 130° C. for 6 hours followed by calcination at 325° C. of 3 hours. The IR spectrum of the catalyst showed two peaks at 960 and 860 $cm^{-1}$, which are characteristic of Keggin structures. Additional peaks corresponding to the $SiO_2$ support were also noted.

The data presented in the following Table exemplify the effectiveness of various embodiments of the process of the invention utilizing the catalysts prepared as described above. The reaction conditions are set forth in the notes to the Table.

TABLE

PROPANE TO ACRYLIC ACID[a]

| CATALYST | T, °C. | P, psig | LIQUID PRODUCTS, mmoles | | GASES, mmoles | | | TO (6 hrs)[b] | |
|---|---|---|---|---|---|---|---|---|---|
| | | | $CH_3CO_2H$ | $CH_2=CHCO_2H$ | $C_3^=$ | CO | $CO_2$ | $C_3^=$ | $CH_2=CHCO_2H$ |
| $H_3PMo_{12}O_{40}$ | 343 | 25 | 1.2 | 0.2 | 2.5 | 3.8 | 2.1 | 0.4 | 0.08 |
| $H_4PVMo_{11}O_{40}$ | 343 | 25 | 1.8 | 0.6 | 8.5 | 6.7 | 5.5 | 1.4 | 0.3 |
| $H_5PV_2Mo_{10}O_{40}$ | 343 | 20 | 3.8 | 0.9 | 10.5 | 20.7 | 15.7 | 1.8 | 0.45 |
| $H_6PV_3Mo_9O_{40}$ | 343 | 55 | 1.6 | 0.3 | 5.0 | 8.6 | 8.7 | 0.8 | 0.13 |
| $H_3PMo_{12}O_{40}/SiO_2/H_2O$ | 345 | 31 | 2.9 | 0.6 | 6.2 | 12.0 | 6.7 | | |
| $H_4PVMo_{11}O_{40}/SiO_2/H_2O$ | 327 | 32 | 4.9 | 0.7 | 8.7 | 10.1 | 6.5 | | |
| $H_5PV_2Mo_{10}O_{40}/SiO_2/H_2O$ | 345 | 40 | 11.6 | 2.0 | 17.4 | 30.0 | 20.2 | 20 | 6.9 |
| $H_6PV_3Mo_9O_{40}/SiO_2/H_2O$ | 344 | 38 | 10.1 | 1.5 | 14.5 | 31.2 | 20.7 | 16 | 6.2 |
| $H_5PV_2Mo_{10}O_{40}/SiO_2$[c] | 350 | 40 | 5.8 | 1.0 | 21.5 | 29.4 | 16.4 | 108 | 5.0 |
| $H_5PV_2Mo_{10}O_{40}/SiO_2/VOSO_4$[c] | 345 | 31 | 11.4 | 1.6 | 18.0 | 25.2 | 17.5 | | |
| $H_5PV_2Mo_{10}O_{40}/SiO_2/VOSO_4$[c] | 362 | 31 | 11.7 | 2.1 | 21.2 | 30.2 | 21.4 | | |
| $H_6PV_2Mo_{10}O_{40}$—S-1[d] | 342 | 25 | 6.7 | 1.8 | 13.2 | 14.5 | 10.8 | 2.2 | 0.9 |
| $H_5PV_2Mo_{10}O_{40}$—S-2[d] | 344 | 25 | 9.1 | 3.1 | 13.6 | 18.2 | 13.4 | 2.3 | 1.6 |
| $H_6PV_2Mo_{10}O_{40}$—S-1[d,e] | 344 | 60 | 4.7 | 1.8 | 4.2 | 14.4 | 8.8 | 1.5 | 0.6 |
| $H_x(Bu_4N)_{5-x}(PFeMo_{11}O_{39})/SiO_2$ | 344 | 32 | 2.0[f] | 0.3[f] | 6.2 | 13.1 | 10.7 | | |

[a]Propane (42 ml/min), Air (25 ml/min) over catalyst ($C_3/O_2/N_2 = 63/7.5/29.5$).
[b]Moles $C_3^=$ or Acrylic Acid produced in 6 hrs per mole POM.
[c]4 ml 30% complex on $SiO_2$ contained 0.2 mmoles complex.
[d]The $H_5PV_2Mo_{10}O_{40}$ complexes designated S-1 and S-2 were prepared at successively higher pH.
[e]Propane (10 ml/min), Air (25 ml/min) $N_2$ (32 ml/min) ($C_3/O_2/N_2 = 15/7.5/77.5$.)
[f]Small amounts of methanol, acetaldehyde and acetone are often formed.

The invention claimed is:

1. A process for the conversion of alkanes to unsaturated carboxylic acids which comprises contacting an alkane with an oxidizing agent and a heteropolyacid comprising:
   (1) at least 9 atoms of a first framework metal or metals comprising molybdenum, tungsten, or vanadium or combinations thereof, and
   (2) at least one atom of a second framework metal or metals comprising independently a metal, is selected from the group consisting of chromium, manganese, rhenium, iron, cobalt, nickel, ruthenium, rhodium, palladium, osmium, iridium, platinum, copper and zinc, or combination thereof;

or polyoxoanion of said heteropolyacid.

2. A process according to claim 1 wherein said second framework metal comprises iron, cobalt, nickel, ruthenium, rhodium, palladium, osmium, iridium, platinum or combination thereof.

3. A process according to claim 2 wherein said second framework metal comprises iron.

4. A process according to claim 1 wherein said polyoxoanion comprises at least one cation.

5. A process according to claim 4 wherein said cation comprises an alkali metal.

6. A process according to claim 5 wherein said cation comprises potassium, sodium or cesium.

7. A process according to claim 6 wherein said cation comprises potassium or sodium.

8. A process according to claim 4 wherein said cation comprises a transition metal.

9. A process according to claim 8 wherein said cation comprises a metal selected from the group consisting of vanadium, chromium, manganese, iron, cobalt, ruthenium and copper.

10. A process according to claim 9 wherein said cation comprises iron.

11. A process according to claim 5 wherein said cation comprises a metal oxo moiety.

12. A process according to claim 11 wherein said metal oxo moiety comprises V=O, Cr=O or U=O.

13. A process according to claim 12 wherein said metal oxo moiety comprises V=O.

14. A process according to claim 1 wherein said heteropolyacid or polyoxoanion is supported on a catalyst support, thereby forming a supported catalyst.

15. A process according to claim 14 wherein said catalyst support is selected from the group consisting of silica, alumina, silica-alumina, carbon, zirconia, titania, ceria and magnesia.

16. A process according to claim 15 wherein said catalyst support comprises silica.

17. A process according to claim 14 wherein said supported catalyst is pre-treated with water prior to use.

18. A process according to claim 17 wherein water comprises 5 to 30 weight percent of said supported catalyst following pretreatment.

19. A process according to claim 14 wherein said supported catalyst is prepared in the presence of vanadyl sulfate.

20. A process according to claim 1 wherein said alkane comprises light alkane comprising three to seven carbon atoms or combinations thereof.

21. A process according to claim 20 wherein said alkane comprises propane and said product comprises acrylic acid.

22. A process according to claim 20 wherein said alkane comprises isobutane and said product comprises methacrylic acid.

23. A process according to claim 1 wherein said conversion is carried out at a temperature in the range from about 225° C. to about 450° C.

24. A process according to claim 23 wherein said temperature is in the range from about 275° C. to about 400° C.

25. A process according to claim 1 wherein said oxidant comprises air or molecular oxygen.

26. A process for the conversion of alkanes to unsaturated carboxylic acids which comprises contacting an alkane with oxidizing agent and a heteropolyacid having the formula $H_e(X_kM_mM'_nO_y)^{-e}$, where X is a Group IIIB, IVB, VB, VIB or transition element; M is independently molybdenum, tungsten, vanadium or combination thereof; M' is independently zinc or a transition metal or combination thereof, wherein M' is different from M, and each M' is bonded through an oxygen atom to another M' atom; k is 1 to 5, n is 2 to 3, m is 5 to 17, and y is 18 to 59; or a polyoxoanion of said heteropolyacid.

27. A process according to claim 26 wherein n is 2.

28. A process according to claim 26 wherein n is 3.

29. A process for the conversion of alkanes to unsaturated carboxylic acids which comprises contacting an alkane with an oxidizing agent and a heteropolyacid having the formula $H_e(X_kM_mM'_3O_y)^{-e}$, where X is a Group IIIB, IVB, VB, VIB or transition element; M is independently molybdenum, tungsten, vanadium or combination thereof; M' is independently zinc or a transition metal different from M or combination thereof; k is 1 to 5, m is 5 to 17, and y is 18 to 59; or a polyoxoanion of said heteropolyacid.

30. A process for oxidizing light alkanes to unsaturated carboxylic acids which comprises contacting an alkane with an oxidizing agent and a heteropolyacid having the formula $H_e(X_kM_mM'_nO_y)^{-e}$, where X is a Group IIIB, IVB, VB, VIB or transition element; M is independently molybdenum, tungsten, vanadium or combination thereof; M' is independently a metal selected from the group consisting of chromium, manganese, rhenium, iron, cobalt, nickel, ruthenium, rhodium, palladium, osmium, iridium, platinum, copper and zinc; k is 1 to 5, n is 1 to 3, n is 5 to 17, and y is 18 to 59; or a polyoxoanion of said heteropolyacid.

31. A process according to claim 26, 29 or 30 wherein said X is selected from the group consisting of phosphorus, silica, gallium, aluminum, arsenic, germanium, boron, cobalt, cerium, praseodymium, uranium and thorium.

32. A process according to claim 26, 29 or 30 wherein said second framework metal is selected from the group consisting of titanium, zirconium, hafnium, niobium, tantalum, chromium, manganese, rhenium, iron, cobalt, nickel, ruthenium, rhodium, palladium, osmium, iridium, platinum, copper and zinc or combinations thereof.

33. A process according to claim 32 wherein said second framework metal comprises iron, cobalt, nickel, ruthenium, rhodium, palladium, osmium, iridium, platinum or combination thereof.

34. A process according to claim 33 wherein said second framework metal comprises iron.

35. A process according to claim 26, 29 or 30 wherein said polyoxoanion comprises at least one cation.

36. A process according to claim 35 wherein said cation comprises an alkali metal.

37. A process according to claim 36 wherein said cation comprises potassium, sodium or cesium.

38. A process according to claim 37 wherein said cation comprises potassium or sodium.

39. A process according to claim 35 wherein said cation comprises a transition metal.

40. A process according to claim 39 wherein said cation comprises a metal selected from the group consisting of vanadium, chromium, manganese, iron, cobalt, ruthenium and copper.

41. A process according to claim 40 wherein said cation comprises iron.

42. A process according to claim 35 wherein said cation comprises a metal oxo moiety.

43. A process according to claim 42 wherein said metal oxo moiety comprises V=O, Cr=O or U=O.

44. A process according to claim 43 wherein said metal oxo moiety comprises V=O.

45. A process according to claim 26, 29 or 30 wherein said heteropolyacid or polyoxoanion is supported on a catalyst support, thereby forming a supported catalyst.

46. A process according to claim 45 wherein said catalyst support is selected from the group consisting of silica, alumina, silica-alumina, carbon, zirconia, titania, ceria and magnesia.

47. A process according to claim 46 wherein said catalyst support comprises silica.

48. A process according to claim 45 wherein said supported catalyst is pre-treated with water prior to use.

49. A process according to claim 48 wherein water comprises 5 to 30 weight percent of said supported catalyst following pretreatment.

50. A process according to claim 44 wherein said supported catalyst is prepared in the presence of vanadyl sulfate.

51. A process according to claim 26, 29 or 30 wherein said alkane comprises light alkane comprising three to seven carbon atoms or combinations thereof.

52. A process according to claim 51 wherein said alkane is propane and said product is acrylic acid.

53. A process according to claim 51 wherein said alkane is isobutane and said product is methacrylic acid.

54. A process according to claim 26, 29 or 30 wherein said conversion is carried out at a temperature in the range from about 225° C. to about 450° C.

55. A process according to claim 54 wherein said temperature is in the range from about 275° C. to about 400° C.

56. A process according to claim 26, 29 or 30 wherein said oxidant comprises air or molecular oxygen.

* * * * *

UNITED STATES PATENT AND TRADEMARK OFFICE
CERTIFICATE OF CORRECTION

PATENT NO. : 5,705,685

DATED : January 6, 1998

INVENTOR(S) :
James E. Lyons, et al.

It is certified that error appears in the above-indentified patent and that said Letters Patent is hereby corrected as shown below:

Column 10, Line 37, the formula "$H_cM''^{+a}_b(X_kM_mM''_nO_y)^{-e}$" should read -- $H_cM''^{+a}_b(X_kM_mM'_nO_y)^{-e}$ --.

Column 12, Line 25, the formula "$H_5PMo_{10}V_{40}/SiO_2/H_2O$" should read -- $H_5PMo_{10}V_2O_{40}/SiO_2/H_2O$ --.

Claim 11, Column 13, line 64, "5" should read --4--.

Signed and Sealed this

Twenty-first Day of July, 1998

Attest:

BRUCE LEHMAN

*Attesting Officer*     *Commissioner of Patents and Trademarks*